United States Patent
Guharay (10) Patent No.: US 8,134,122 B2
(45) Date of Patent: Mar. 13, 2012

(54) MULTI-MODAL PARTICLE DETECTOR

(75) Inventor: Samar K. Guharay, Fairfax Station, VA (US)

(73) Assignee: The Mitre Corporation, McLean, VA (US)

( * ) Notice: Subject to any disclaimer, the term of this patent is extended or adjusted under 35 U.S.C. 154(b) by 0 days.

(21) Appl. No.: 12/689,825

(22) Filed: Jan. 19, 2010

(65) Prior Publication Data
US 2012/0032071 A1 Feb. 9, 2012

Related U.S. Application Data

(62) Division of application No. 12/076,633, filed on Mar. 20, 2008.

(51) Int. Cl.
*G01N 23/00* (2006.01)
(52) U.S. Cl. ........ 250/287; 250/286; 250/288; 250/425; 422/68.1; 422/73; 436/110; 73/23.35; 73/865.8
(58) Field of Classification Search ................. 422/68.1, 422/100
See application file for complete search history.

(56) References Cited

U.S. PATENT DOCUMENTS

| | | | |
|---|---|---|---|
| 4,378,499 A | 3/1983 | Spangler et al. | |
| 4,390,784 A | 6/1983 | Browning et al. | |
| 4,777,363 A | 10/1988 | Eiceman et al. | |
| 4,987,286 A | 1/1991 | Allen | |
| 5,668,342 A | 9/1997 | Discher | |
| 5,866,430 A * | 2/1999 | Grow ................................. | 506/6 |
| 6,610,977 B2 * | 8/2003 | Megerle ........................ | 250/287 |
| 6,969,851 B1 | 11/2005 | Sheen et al. | |
| 7,361,311 B2 * | 4/2008 | Cooks et al. ................... | 250/284 |
| 7,530,257 B2 * | 5/2009 | Bonne ........................... | 73/23.25 |
| 2009/0238723 A1 | 9/2009 | Guharay et al. | |

OTHER PUBLICATIONS

Asbury et al., Analysis of explosives using electrospray ionization/ion (ESI/IMS), Elsevier Science B.V., Talanta, 50, (2000), pp. 1291-1298.
Matz et al., "Evaluation of suspected interferents for TNT detection by ion mobility spectrometry", Elsevier Science B.V., Talanta, 54, (2001), pp. 171-179.
Tang et al., "High-Sensitivity Ion Mobility Spectrometry/Mass Spectrometry Using Electrodynamic Ion Funnel Interfaces", Anal. Chem. 77, (2005), pp. 3330-3339.
http://www.process-instruments-inc.com/pages/energetics.html, printed on Mar. 10, 2008, pp. 1-9.

* cited by examiner

*Primary Examiner* — Sally Sakelaris
(74) *Attorney, Agent, or Firm* — Sterne, Kessler, Goldstein & Fox P.L.L.C.

(57) ABSTRACT

Systems, methods and computer program products for the multi-modal detection of particles are described herein. An embodiment of the present invention is a particle detector that includes a first chamber wherein analyte particles are subjected to a first particle detection mechanism, and a second chamber coupled to the first chamber, wherein the analyte particles are subjected to a second particle detection mechanism, and wherein the detection characteristics of second particle detection mechanism are orthogonal to detection characteristics of the first particle detection mechanism. According to another embodiment, the present invention is a particle detection method including the steps of detecting presence of at least one predetermined particle type in an analyte particle sample using a first particle detection mechanism, and confirming the presence of the predetermined particle type in the analyte particle sample using a second particle detection mechanism, wherein detection characteristics of the second particle detection mechanism are orthogonal to detection characteristics of the first detection mechanism.

12 Claims, 7 Drawing Sheets

MULTI-MODAL PARTICLE DETECTOR

CROSS-REFERENCE TO RELATED APPLICATIONS

This application is a divisional of U.S. Non-Provisional application Ser. No. 12/076,633 filed Mar. 20, 2008, which is hereby incorporated by reference in its entirety.

BACKGROUND OF THE INVENTION

1. Field of the Invention

The present invention relates generally to threat detectors, and more particularly to multi-modal particle detectors for detecting chemical, biological, and explosives threats.

2. Background Art

The detection of chemical, biological, and explosives threats is becoming increasingly difficult due to the continuously changing nature of such threats. For example, new combinations of chemicals are used for explosives, new delivery mechanisms are used with lethal chemical and biological compounds, and new constructions are employed for improvised explosives devices (IED). Detection is also made difficult due to threats arising in environments or locations that are not conducive for deploying traditional threat detection mechanisms.

Many threat detection devices are described in the art. For example, the background section of U.S. Pat. No. 6,610,977 ('977 patent), which is incorporated herein by reference in its entirety, includes an extensive description of various threats and threat detection mechanisms. Generally, threat detection mechanisms may be classified into trace and bulk detection. In trace detection, minute quantities of materials are detected either in vapor or particulate form. The related trace detection mechanisms include electron capture, gas chromatography, mass spectroscopy, ion mobility spectrometry, Raman spectroscopy, plasma chromatography, biological markers and laser photo acoustics. Trace detection mechanisms are primarily suited for detection of threat substances in the environment. Bulk detection mechanisms are primarily used to detect bulk quantities of threat substances that are concealed and carried in various forms, including baggage. They include x-ray, gamma-ray, neutron activation and nuclear magnetic resonance.

Despite the large number and variety of threat detectors that are commercially available, there is a paucity of multi-modal detectors that are capable of detecting multiple threats based on different properties of threat particles. To be effective, multi-modal detectors must detect threat particles efficiently and with reduced false alarm rates for a variety of threat particles, while also being capable of flexible deployment in various environments. Some attempts at developing multi-modal detectors have been made. For example, the '977 patent discloses a combination of multiple known detectors in a predetermined decision hierarchy. U.S. Pat. No. 5,668,342 ('342 patent) discloses a method of detecting multiple types of explosives materials by illuminating that material with multiple energy sources. The '977 patent combines different sensors as they are without an effort to increase the efficiency available by integration of selected techniques, and without an effort to increase the ability to deploy. The '342 patent only addresses the detection and neutralization of explosives in baggage check applications.

What is needed therefore, is a multi-modal particle detector that is capable of efficiently detecting multiple types of threats including chemical, biological, and explosives threats with reduced false alarm rates, and is capable of being deployed reliably in a number of different environments.

BRIEF SUMMARY OF THE INVENTION

The present invention is directed to systems, methods and computer program products for multi-modal particle detectors. Briefly stated, a particle detector system embodiment of the present invention includes a particle detector that includes a first chamber wherein analyte particles are subjected to a first particle detection mechanism, and a second chamber, coupled to the first chamber, wherein the analyte particles are subjected to a second particle detection mechanism, and wherein the detection characteristics of second particle detection mechanism are orthogonal to detection characteristics of the first particle detection mechanism.

According to another embodiment, the present invention is a particle detection method including the steps of detecting presence of at least one predetermined particle type in an analyte particle sample using a first particle detection mechanism, and confirming the presence of the predetermined particle type in the analyte particle sample using a second particle detection mechanism, wherein detection characteristics of the second particle detection mechanism are orthogonal to detection characteristics of the first detection mechanism.

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The features and advantages of the present invention will become more apparent from the detailed description set forth below when taken in conjunction with the drawings. In the drawings, like reference numbers generally indicate identical, functionally similar, and/or structurally similar elements.

DETAILED DESCRIPTION OF THE INVENTION

1. Overview

The present invention relates to embodiments of multi-modal detectors for the detection of multiple threats. While the present invention is described herein with reference to illustrative embodiments for particular applications, it should be understood that the invention is not limited thereto. Those skilled in the art with access to the teachings herein will recognize additional modifications, applications, and embodiments within the scope thereof and additional fields in which the invention would be of significant utility.

A key to effective multi-modal threat detection and reduction of false alarms is the use of multiple detection mechanisms in an efficient and integrated manner. For example, embodiments of the present invention integrate the use of ion mobility spectrometry (IMS) detection with surface enhanced Raman spectroscopy (SERS). The two particle detection mechanisms, IMS and SERS, are selected due to the orthogonal detection properties of each mechanism. For example, IMS detection is based on mobility properties of particles, while SERS detection is based on the light scattering properties. By combining orthogonal detection characteristics, the efficiency of detection and also the range of threat substances detectable are increased.

IMS technology is generally well known in the art. Similarly, the construction of a standalone IMS particle detector is well known. For example, U.S. Pat. No. 6,969,851, which is incorporated herein by reference in its entirety, outlines the construction of an IMS sensor for detecting a particular gaseous substance. An IMS detector includes an ionization region and a drift region. A shutter grid is placed between the two regions so that the flow of analyte particles from the ionization region to the drift region can be controlled. Analyte particles are ionized in the ionization region. Subsequently samples of ionized analytes make their way through the shutter grid into the drift region. Ionized analytes are accelerated in the drift cell by an electric field and are simultaneously slowed down due to collisions with the background drift gas. This results in a characteristic drift time for a specific analyte module. Detection, for example, collector electrodes at the end of the drift region, is triggered when the ionized particles strike the electrodes. A current may be generated in proportion to the number of ionized particles striking the collector electrodes at a given instant. IMS measures the drift time of each particle, which is defined by the time interval between the particle entering the drift chamber 122 and arrival at the collector electrodes 124. The characteristic drift times for a variety of particle types may be known to the device through reference data.

SERS technology and the construction of a standalone SERS detector are also well known in the art. A SERS detector, in general, includes a light source, an optical light collection and detection mechanism, and a SERS substrate upon which analyte particles are accumulated and upon which a photon beam generated by the light source is irradiated. The scattered light from the vibrationally excited analyte molecules on the SERS substrate surface is monitored by the optical detection mechanism to detect the characteristic Raman spectra typical to known particle types. Raman spectroscopy is a mechanism that measures the inelastic scattering of optical (photon) energy resulting in a shift in the frequency of the incident light and thus resulting in spectral peaks that correspond to photon energy different from those of the energy of the incident photons on the analyte particles. The scattered Raman signals arise as a result of changes (with respect to time) in polarization in particles due to vibrational excitation of the molecules by the incident light, yielding unique and characteristic structurally-specific Raman signal fingerprints to most particles. The intensities of Raman bands are substantially dependent on the intensity of the local electric field and the number of particles with the corresponding vibration state. Also, due to very narrow line-width of natural Raman spectral lines the inherent high resolution of Raman spectra allows the simultaneous analysis of multiple particle types. SERS is a variant of Raman spectroscopy that yields highly enhanced Raman signals due to the special engineering of the substrates and has the requisite sensitivity to detect particles in small or trace quantities of samples, without multiple passes of the analytes through the detection mechanism or long acquisition times. A detector, such as the present invention in one embodiment, due to its small size, ease of deployment, and portability must have a high level of sensitivity even to small sample quantities. SERS methods allow analyte particles to be adsorbed into substrates including nanometer-size metallic particles like silver, copper and gold, which substantially enhances the intensity of the scattered Raman light, thus making it practical to obtain characteristic Raman fingerprints for particles with small sample quantities.

By combining detection mechanisms with highly orthogonal detection characteristics, such as but not limited to those described herein, embodiments of the present invention minimize the risks of false detection and faulty identification. Furthermore, by placing an IMS detector in front of a SERS detector, embodiments of the present invention are designed to utilize IMS as a speedy filtering mechanism and to selectively subject identified samples for the more rigorous SERS detection. Threat particles that cannot be sufficiently distinguished using only IMS may be distinguished by using both its IMS characteristics and SERS characteristics. By activating SERS detection only as needed, embodiments of the present invention leverage the relatively more sensitive SERS detection equipment in an efficient manner. Embodiments of the present invention may be constructed in miniaturized form and in other forms suitable for portability and deployment in various environments including environments demanding unmanned deployment.

Example embodiments for achieving multi-modal threat detection according to the present invention are described in the following sections.

2. Composition of the Multi-Modal Detector

Figure 1:
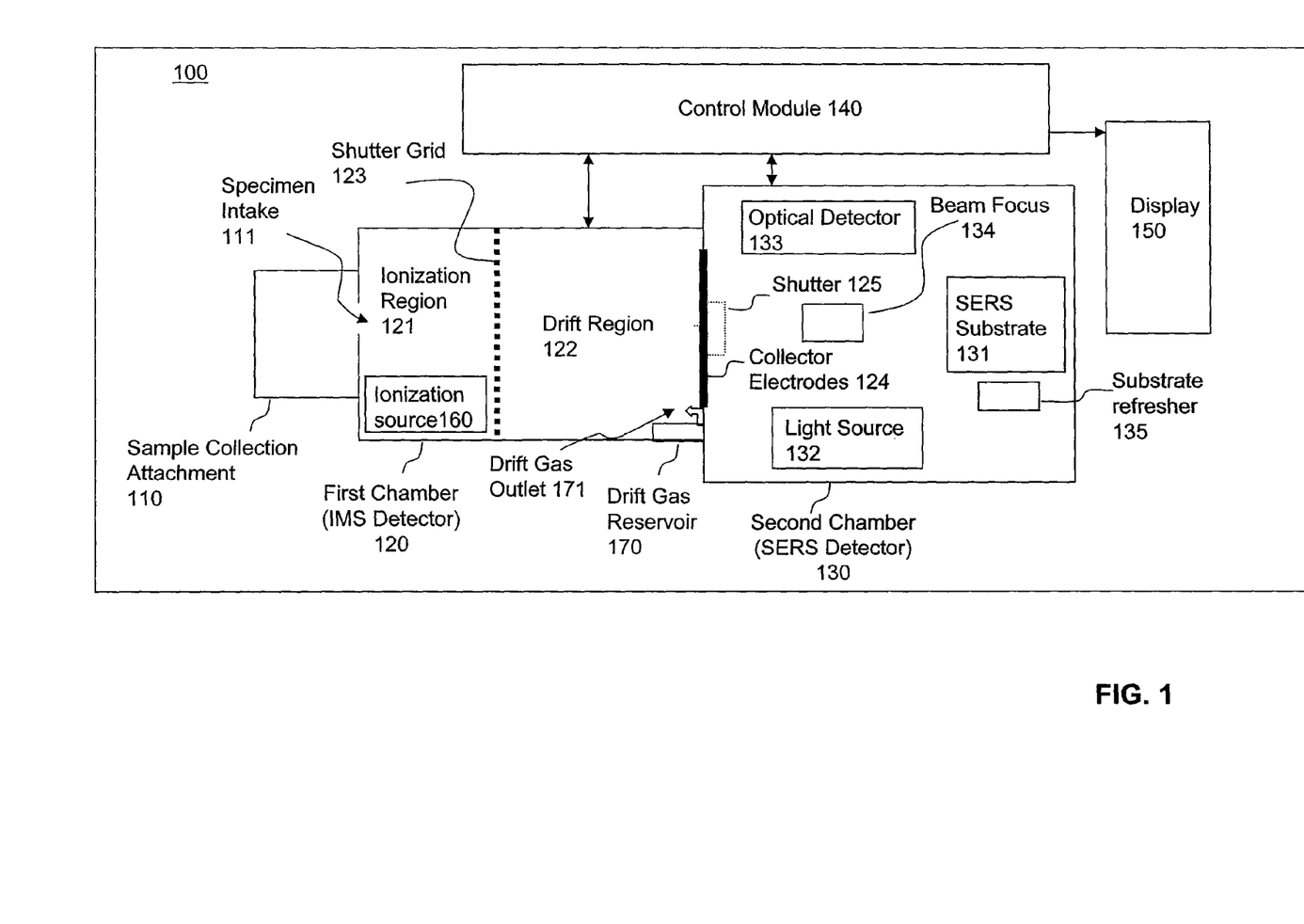
FIG. 1 is a multi-modal detector according to an embodiment of the present invention.

FIG. 1 illustrates a multi-modal particle detector 100 according to an embodiment of the invention. Example multi-modal detector 100 includes an IMS particle detector in a first chamber 120 and a SERS detector in a second chamber 130. Sample analytes subjected to IMS detection in the first chamber 120 may be selectively subjected to further SERS detection in the second chamber 130.

The first chamber 120 includes an ionization region 121 and a drift region 122. The ionization region 121 includes a specimen intake 111 where the analyte specimen is introduced into the IMS detector 120 and an ionization source 160. The ionization source 160 may include a radio active substance such as nickel-63 ($^{63}Ni$), an electrospray ionizer, or a spark electrode ionizer. An optional sample collection attachment 110 may be integrated to detector 100 which includes a vacuum pump or similar suction device to assist in the collection of the analyte sample from the environment. The sample can also be obtained by swiping the surface of the threat object (that needs to be examined) or by additional means that allow releasing particles from a surface, such as by impinging an air jet, by striking strobe light or other electromagnetic pulses such as terahertz radiation. The drift region 122 may include collector electrodes 124 that measure particles, a drift gas reservoir 170, and a drift gas outlet 171. A shutter grid 123 separates the ionization region 121 from the drift region 122 and includes the capability to allow controlled amounts of ionized samples into the drift region 122. When shutter grid 123 is open analytes enter from the ionization region 121 and flow through the drift region 122 under the guidance of an electric field. A drift gas, collected in the drift gas reservoir 170 and injected into the drift region 122 through the drift gas outlet 171, flows in the direction opposite to the analyte particles. Analyte particles travel through the drift region 122 at speeds characterized by particle type and collide with the collector electrodes 124 that generate an electrical signal proportional to the intensity of the particle collisions. The IMS characteristics of the analyte particles are determined based on the signal generated by the collector electrodes 124. The collector electrodes 124 may include a shutter mechanism whereby particles are allowed into the second chamber 130 in controlled time intervals. For example, in one embodiment, instead of having particles collide with the collector electrodes 124, the collector electrodes 124 may momentarily move apart to uncover shutter 125 which is an opening to the second chamber 130.

The second chamber 130 includes a SERS substrate 131, a light source 132, and an optical detector 133. The SERS substrate 131, is generally placed at the far end from shutter 125. In another embodiment, the SERS substrate 131 may be placed on a precision position manipulation platform that may, for example, be controlled by the control module 140 such that detection is optimized. The light source 132 may include a krypton-ion laser, near infrared diode laser, or Nd:YAG laser that generates light signals having wavelengths in the range, by way of example and without limitation, from 532 to 1064 nm. Optionally, a beam focusing device 134 and a substrate refresher device 135 may be included. Beam focusing device 134 can be used to focus the ion beam such that particle concentration on localized areas on the SERS substrate is enhanced. A method, such as, for example, the well known methods of focusing with electrostatic quadrupole lenses or ion beam funneling can be used in device 134. Ion beam funneling is described, for example, in Keqi Tang, Alexandre A. Shvartsburg, Hak-No Lee, David C. Prior, Michael A. Buschbach, Fumin Li, Aleksey V. Tolmachev, Gordon A. Anderson, and Richard D. Smith, "High-Sensitivity Ion Mobility Spectrometry/Mass Spectrometry Using Electrodynamic Ion Funnel Interfaces," Analytical Chemistry, pp. 3330-3339 Vol. 77 (2005). The optional substrate refresher device 135 can enhance the reusability of the SERS substrate. For example, device 134 can utilize a technique to releasing particulates such as, for example, use of an air jet, use of an energy transfer medium including water droplets or a mixture of water and alcohol, and dry removal by laser. A method of dry removal by laser is described in U.S. Pat. No. 4,987,286 that is incorporated by reference herein in its entirety. Embodiments of the present invention may include additional optical devices or mechanisms to focus the light beam between the light source 132 and SERS substrate 131, and also to enhance signal detection between SERS substrate 131 and optical detector 133. When the light source 132 is active and focused on the SERS substrate 131, analytes that collide with the SERS substrate 131 emit Raman signals that are then detected by the optical detector 133.

Figure 2:
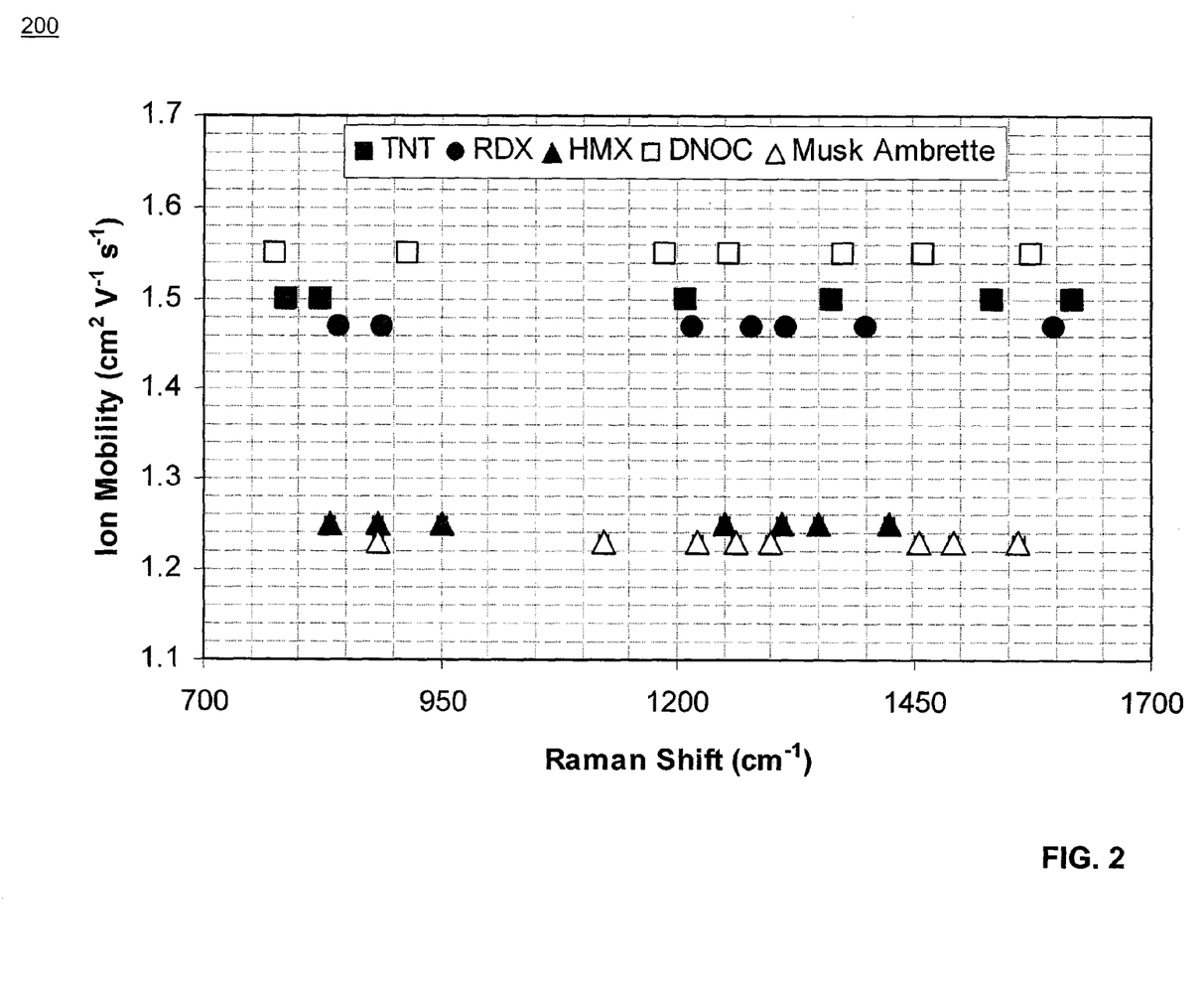
FIG. 2 is an example graph showing the effectiveness of combining highly orthogonal detection mechanisms, specifically IMS and SERS. The graph of FIG. 2 may be derived, for example, from the output of a multi-modal detector of FIG. 1.

Both detectors, the IMS detector in the first chamber 120 and the SERS detector in the second chamber 130, of the example multi-modal particle detector 100, may be coupled to a control module 140. The control module 140 may control and coordinate events in the first chamber 120 and the second chamber 130. The control module 140 may also receive particle data from both detectors and combine and analyze the received particle data. For example, the received particle data may be combined in a manner that increases the likelihood of definitive identification of analyte particles. The combined results may be displayed in an optionally coupled display 150. FIG. 2 illustrates an example graph 200 that may be displayed on display 150. Graph 200 shows five analyte compounds with their characteristics plotted according to the characteristic ion mobility values from IMS detection on the Y-axis, and according to the characteristic Raman shift values from SERS detection on the X-axis.

The control module 140 may control, for example, the specimen intake 111 to control when sample analytes are input and in what quantity, the ionization source 160 to control when analyte samples are ionized, the shutter grid 123 to control the timing and volume of ionized samples allowed into the drift region 122, the activation and strength of the electric field in the drift region 122, the acquisition of drift gas in component 170, the injection of drift gas through outlet 171, the monitoring of the collector electrodes 124 to measure the signal generated, the manipulation of the collector electrodes 124 and shutter 125 to allow analyte particles to flow through to the second chamber 130 at controlled intervals, the activation of the light source 132, and the monitoring of the optical detector 133 to measure and identify the Raman spectra that are generated. Identification may require cross-checking the measured spectra with a reference spectral library. Also, the control module 140 may include control logic for combining the signals generated from the IMS detector's collector electrodes 124 and the SERS detector's optical detector 133. Control module 140, in embodiments of the present invention, may be coupled to the first chamber 120, second chamber 130, and display 150 through wired or wireless communication channels and also may be distributed over multiple platforms.

Figure 3:
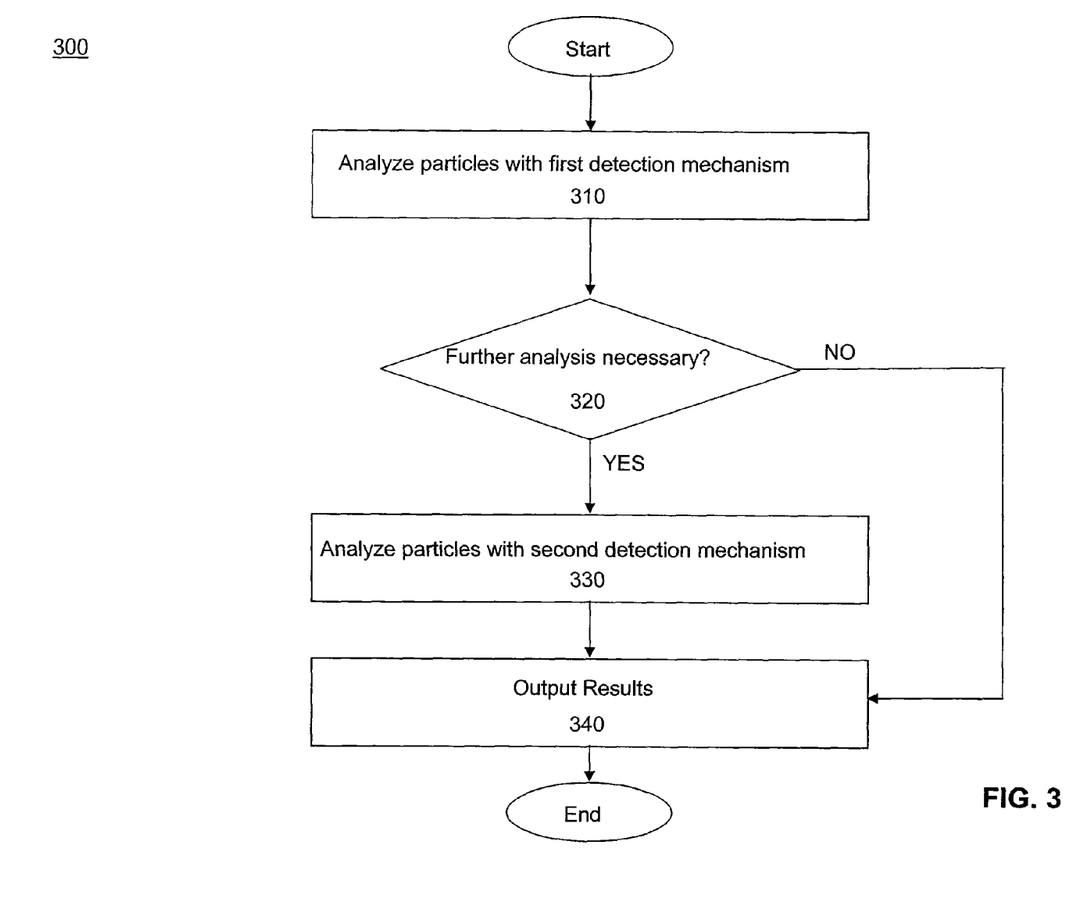
FIG. 3 is a flowchart illustrating the operation of a multi-modal detector according to an embodiment of the present invention.

The operation of this embodiment shall now be described in greater detail with reference to flow charts 300, 400, 500, and 600 in FIGS. 3, 4, 5 and 6 respectively. For illustrative but non-limiting purposes, the flowcharts 300, 400, 500, and 600 shall be described with continuing reference to the example multi-modal particle detector 100. Flowchart 300 of FIG. 3 illustrates the overall operation of the multi-modal particle detector 100. In step 310 samples of the analyte particles are first subjected to IMS detection in the first chamber 120. Further details of processing in step 310 are described below with respect to flowchart 400. The resulting particle data from IMS detection is received by control module 140 and a determination may be made, in step 320, if further analysis of the analyte is required. The determination in step 320 may be based on the particular IMS measurements being observed, analysis of the measured data and cross checking with a reference library of mobility values. For example, if the IMS measurement corresponds to an ion mobility value of approximately $1.5\ cm^2 V^{-1} s^{-1}$ in a sample for air or nitrogen as drift gas, the control module 140 may determine that it is not possible to clearly determine if the analyte substance is a threat substance such as TNT or RDX or a non-threat substance such as dinitro-o-cresol (DNOC) unless a laboratory-scale high-resolution IMS is used. If it is determined in step 320 that further analysis is necessary, then in step 330 samples of the analyte are subjected to SERS detection in the second chamber 130. A detailed description of processing within a SERS detector is provided below with respect to flowchart 500. The resulting particle data of the SERS detection is received by control module 140. Control module 140 combines the IMS particle data and the SERS particle data. In step 340 control module 140 may output the combined particle data to display a combined graph on display 150. Graph 200 of FIG. 2 is an example graph that integrates IMS particle data and SERS particle data in such a manner as to facilitate definitive determination of the analyte particles.

3. IMS Detection in the Multi-Modal Detector

Figure 4:
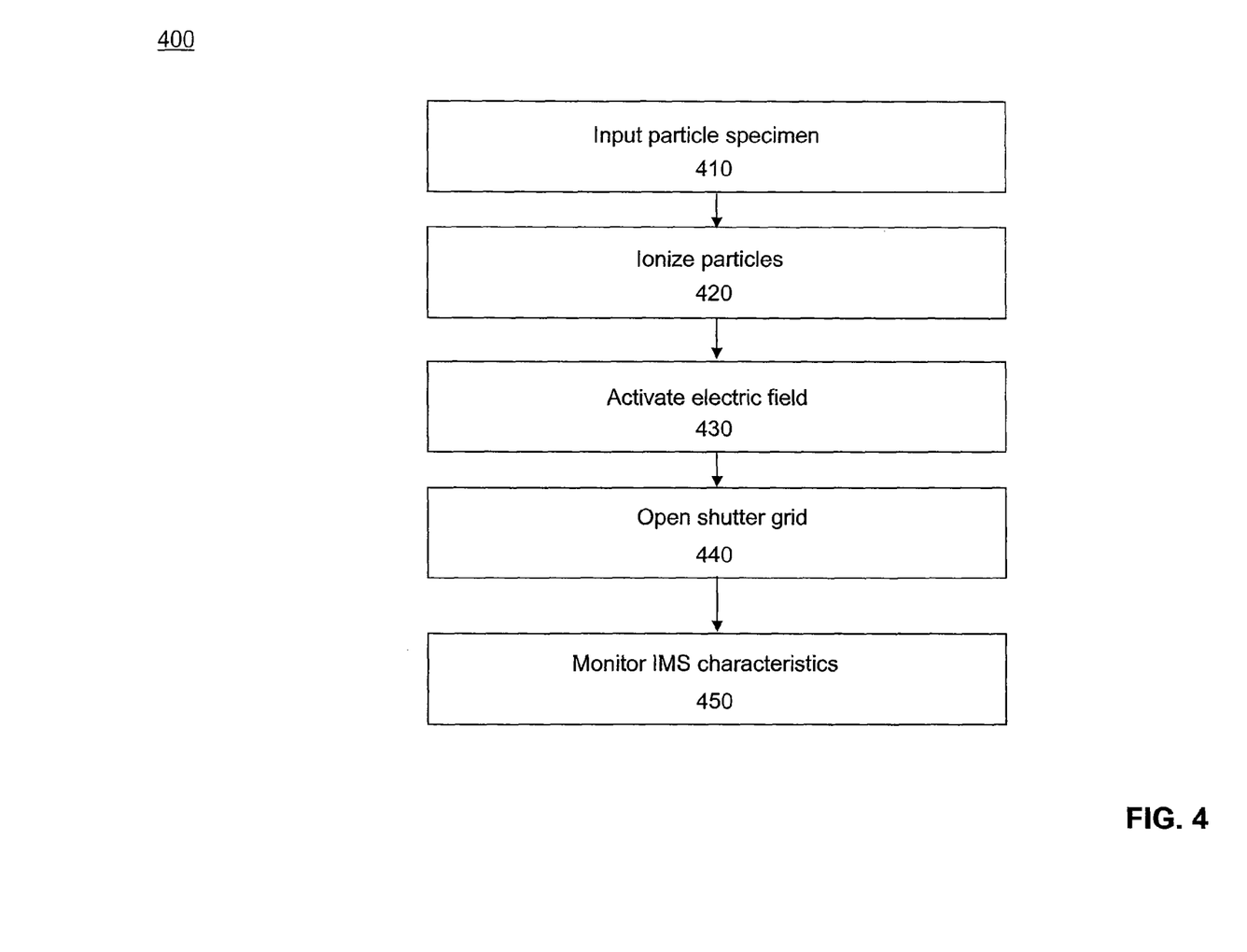
FIG. 4 is a flowchart illustrating the operation of an IMS component of a multi-modal detector according to an embodiment of the present invention.

In FIG. 4, the flowchart 400 illustrates the processing within the IMS detector in the first chamber 120 of the multi-modal detector 100. In step 410 an analyte sample is input to the EMS detector's ionization region 120 through specimen intake 111. Embodiments of the present invention may include a sample collection attachment 110. It should be noted that there are many well known methods of acquiring a suitable analyte sample to be input through specimen intake 111. For example, if the analyte particles are airborne in the environment, an adequate specimen may be collected with or without the aid of a vacuum pump or similar environment air suction device implemented in an optional sample collection attachment 110. In another embodiment of the present invention, a heating element placed in the sample collection attachment 110 may be used to release analyte particles from a specimen into specimen intake 111.

In step 420, particles in the ionization region 121 are ionized. In some embodiments, an ionization source 160 is used. One of several ionization sources 160 may be used to achieve the ionization of analyte particles. For example, a radio active substance such as nickel-63 ($^{63}$Ni) may be used, where the β-particles released by $^{63}$Ni collide with particles in the sample, such as nitrogen and oxygen. The ionized particles then react with the analyte particles being examined, and analyte ions are formed. In another embodiment, a soft ionization technique, for example, electrospray ionization may be utilized where less fragmentation of analyte particles occur. In yet another embodiment of the present invention, ionization may be caused by the use of an electric discharge. For example, the ionization region 121 may have as the ionization source 160 a spark electrode coupled to a voltage source that enables the creation of spark discharge. The spark discharge triggers ionization of analyte particles along with other particles of the specimen. U.S. Pat. No. 6,969,851, incorporated herein by reference in its entirety, includes an implementation of ionization by the use of an electric discharge. Other ionization techniques that may be used in embodiments of the present invention include photo-ionization, corona discharge ionization and ionization by the use of an electric discharge. Ionization techniques and the implementation thereof are well known in the art.

In step 430, an electric field may be activated. The electric field may, for example, exist between the left wall of the ionization region 121 and the right wall of the drift region 122. The electric field is substantially uniform. A purpose of the electric field is to encourage the movement of the ionized analytes from the ionization region 121 into the collector electrodes 124 in the drift region 122. In another embodiment, the electric field may exist between the left and right walls of the drift region 122. U.S. Pat. No. 4,378,499, incorporated herein by reference in its entirety, describes methods of generating an electric field.

The shutter grid 123 is opened in step 440 to allow ionized analytes to enter the drift region 122. For example, in the embodiment illustrated in multi-modal detector 100 the ionized particles may be kept in the ionization region 121 by biasing the inside of the ionization region 121 and the shutter 123 with the same polarity as the ionized particles. When a sample of the ionized particles is to be released into the drift region 122 the shutter grid 123 may be momentarily biased with the opposite polarity so that the ionized particles are drawn towards it. The direction of electric field is appropriately established so that the analyte ions of a particular polarity can pass through the shutter grid and are accelerated in the drift cell. The shutter grid is then opened allowing the ionized particles to move into the drift region. The shutter is generally made of thin mesh wires with a bias voltage between them. When the bias voltage is turned on, the ions are attracted to the gate and lose their charge. When the bias voltage is turned off, the ions are released into the drift region. U.S. Pat. No. 4,777,363, incorporated herein by reference in its entirety, discloses a particular type of ion-gate known as a Bradbury-Nielson arrangement which may be used in an embodiment of the present invention. In another embodiment of the present invention, the shutter grid 123 may be an electro-mechanical device operated by an electrical pulse where the analyte particles are drawn to the drift region 122 due to the electric field in the drift region 122.

Analyte particles flowing into the drift region 122 through the open shutter grid 123 move across the drift region 122. The analyte particles in drift region 122 move parallel to a uniform electric field in the drift region 122. At the opposite end from the shutter grid 123, the analyte particles make contact with the collector electrodes 124. The drift region 122 may have a length of about 8 cm and may have a substantial electric field, for example, of several hundred volts per centimeter. In one embodiment, the drift region 122 is 4 cm in length and 3 cm in diameter. The particles, guided by the electric field in the drift region 122, arrive at the collector electrodes 124. The electric field in the drift region 122 is substantially uniform. Generally, particles travel at a speed that is determined by their size, mass and geometry, and further affected by the specific drift medium including the electric field within the drift region 122. In general, smaller ions travel faster than the larger ions, as they traverse the drift region and collide with the collector electrodes 124. For each IMS device, in general the drift time for each type of particle is known. The current generated at collector electrodes 124 is proportional to the number of ions that collide over time. The collector electrodes 124 in the embodiment illustrated in multi-modal detector 100 may be implemented as a Faraday plate. For example, U.S. Pat. No. 4,390,784, incorporated herein by reference in its entirety, discloses a particular design of collector electrodes 124. In general, a processor may monitor the signal generated by the collector electrodes 124 to determine the type of particles based on the drift duration of each particle colliding with the collector electrodes 124. For example, the strength of the electrical signal generated over time, when related to the expected drift time of each particle type will yield a measure of the composition of particles contained in the sample. In step 450, the IMS characteristics of analyte samples are monitored using methods including, for example, the monitoring of the current generated by the collector electrodes 124.

Within the drift region 122, the ionized particles interact with drift gas particles that are separately injected into the drift region 122. The drift gas may be clean dehumidified air. In one embodiment of the present invention, a drift gas inlet 171 is situated below the collector electrodes 124. The drift gas inlet 171 may be connected to a drift gas acquisition device 170. In the example embodiment illustrated in multi-modal detector 100, drift gas acquisition device 170 may be a device that dehumidifies and filters air obtained from the environment. The drift gas, injected from the drift gas inlet 171, flows in the direction opposite to analyte particles. The drift gas may pass through shutter grid 123 in the direction opposite to analyte particles and exit the ionization region 121 through specimen intake 111. A person skilled in the art will understand that many alternative designs are possible for the drift gas inlet 171 and drift gas acquisition device 170.

In an embodiment of the present invention, the capability exists to operate the IMS detector in a mode where the analytes are collected at the collector electrodes 124 or in a mode where the analytes are allowed to bypass the collector electrodes 124 to the SERS detector and enter the second chamber 130 through shutter 125. An embodiment of the present invention includes the ability to use the IMS detector in the first chamber 120 to make a preliminary determination of the level of interest in the sample being analyzed, and if the sample meets certain criteria of interest, for example, having IMS detect the presence of a composition of analyte particles as determined by comparing the mobility value from the measured IMS data with that from the reference library, to enable further analysis using SERS in the second chamber 130. Due to the orthogonal nature of IMS and SERS detection characteristics, further analysis using SERS would confirm, in many cases, the composition of analyte particles initially determined using IMS. One aspect of the efficiency of the multi-modal detector 100 is the use of IMS detection equipment as a filter to limit the use of SERS detection equipment. In general, IMS equipment can yield high sensitivity and rapid response times, and are robust to use, whereas SERS equipment have high sensitivity, high chemical specificity, and lower robustness. To facilitate the passage of the analyte particles to the second chamber 130, the collector electrodes 124 may be momentarily moved to expose shutter 125 at the instruction of the control module 140. In another embodiment of the present invention, a separate path may be provided to inject particles into the second chamber 130 upon instruction by the control module 140. For example, a separate path may be constructed from the analyte intake region 111 to the second chamber 130 that bypasses the IMS drift region 122.

Control module 140 may be configured to allow the passage of certain analyte particles from the first chamber 120 to the second chamber 130. Only an analyte sample likely to contain a predetermined set of particles, as determined by the IMS detector in the first chamber 120, may be allowed into the second chamber 130. This allows the SERS detector in the second chamber 130 to be activated only as needed to analyze initial determinations made by the IMS detector in the first chamber 120.

4. SERS Detection in the Multi-Modal Detector

Figure 5:
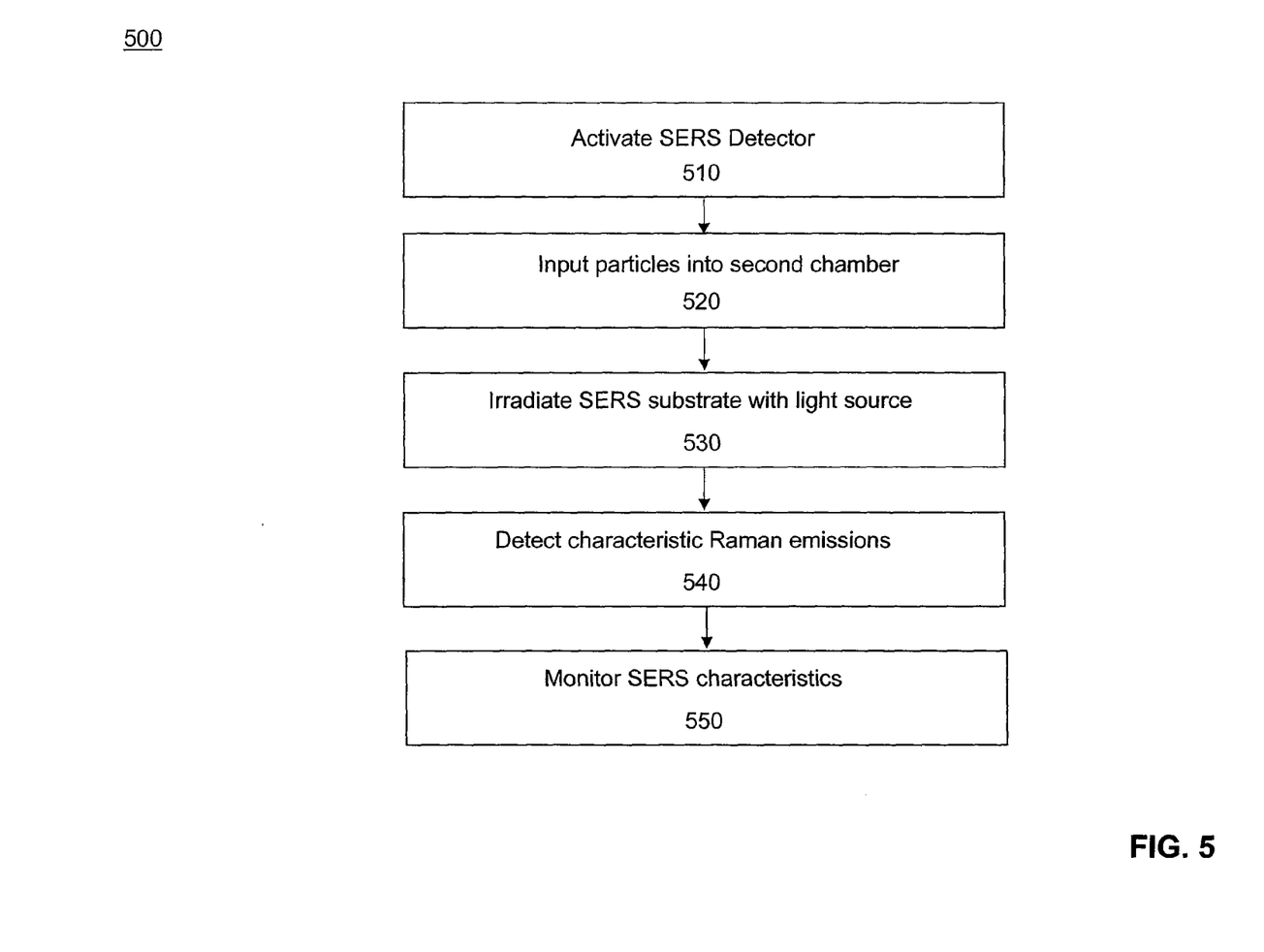
FIG. 5 is a flowchart illustrating the operation of a SERS component of a multi-modal detector according to an embodiment of the present invention.

In FIG. 5, the flowchart 500 illustrates the processing within the SERS detector in the second chamber 130 of the multi-modal detector 100. When a determination is made in step 320 that further analysis of the analyte sample is required, control module 140 may, in step 510, activate the SERS detector in the second chamber 130. For example, the light source 132 may be activated, the SERS substrate may be heated, and optical detector 133 may be focused prior to the entry of the analytes into the second chamber 130 from the first chamber 120. In step 520 analyte particles are allowed into the second chamber 130. Analyte particles flow through into the second chamber 130 and deposit on the SERS substrate 131. In step 530, light source 132 is irradiated on the SERS substrate. Analytes that are present on the SERS substrate 131 when light source 132 is irradiated get vibrationally excited due to the enhanced local electric field at the SERS substrate 131 and generate characteristic Raman signals. In step 540, Raman signals are detected at optical detector 133. A person skilled in the art will understand that some embodiments of the present invention may include devices to enhance detection, for example, focusing lenses or collimating lenses, as intermediate devices between the SERS substrate 131 and optical detector 133. Some embodiments of the present invention may also include intermediate collection optical fibers between the SERS substrate 131 and optical detector 133, as well as filters that reduce background fluorescent light. Optical detector 133 generates a signal indicative of the spectral components detected in the Raman signals. In step 550, the SERS characteristics of the analyte particles may be monitored through Raman signals received at optical detector 133. The output signal representing the detected spectral components, generated by the optical detector 133, may be received by control module 140. The control module 140 may further filter secondary Raman signals and noise from the submitted signal, for example, by the execution of a software computer program. The control module 140 may further ascertain the specific type of particles contained in the sample. For example and without limitation, software programs may be used to analyze the Raman signals to determine the specific mix of analytes contained in the sample of particles.

Light source 132 may be implemented as a krypton-ion laser, near infrared diode laser, or Nd:YAG laser that generates light signals having wavelengths in the range, by way of example and without limitation, from 532 to 1064 nm. In one embodiment, for example as in multi-modal detector 100, a 785 nm laser with a milliwatt power level may be used. The light signal generated by light source 132 is focused on the surface of SERS substrate 131. A person skilled in the art will understand that, in some embodiments of the present invention, there may be, for example, an optical fiber between light source 132 and SERS substrate 131 to guide the light signal and/or a filter or lens to focus the light signal on to the SERS substrate 131.

5. Control of the Multi-Modal Detector

Control module 140 directs the operation of multi-modal detector 100. For example, processing in control module 140 may include triggering the opening of shutter grid 123 and collector electrodes 124, controlling the activation of the ionization source 160, regulating the drift region 122 electric field, activating the light source 132, and the collection of analyte information from collector electrodes 124 and optical detection device 133. Control module 140 may have access to characteristic IMS drift times as well as characteristic Raman spectra for a plurality of analyte particle types. Analyte data received from the collector electrodes 124 and optical detector 133 may be matched against known characteristic IMS drift times and Raman spectra to make determinations. Control module 140 includes control logic to receive, combine and analyze particle data from the IMS detector in the first chamber 120 and the SERS detector in the second chamber 130. The combination of the results received from the two detectors enable the presentation of that data in such a way as to distinguish the components contained in the analyte sample. The functionality of the control module 140 may be implemented in software and executed on one or more processors. In some embodiments, control module 140 may include hardware or firmware components to assist in some of the processing. For example, the collection of the SERS detected Raman spectra and the matching of the collected spectra to the predefined spectra may be performed by a specialized processor. In yet another embodiment of the present invention, the first chamber 120 and the second chamber 130 may each have its own dedicated processor to control the respective detection mechanism and collect analyte data. The data may then be combined to produce a combined graph.

Control module 140 may also control a display 150. Display 150 may display a two-dimensional graph of properties of each analyte type. In one embodiment of the present invention, the two dimensional graph of FIG. 2 may be generated by control module 140 and displayed in display 150. Graph 200 illustrates one clear advantage of the present invention—that of being able to clearly differentiate between analytes that may display very similar characteristics in one detection mechanism. For example, in graph 200, TNT, RDX and DNOC display very close IMS drift times as indicated on the Y-axis, but have substantially different Raman characteristics. Similarly, HMX and musk ambrette (a common ingredient in perfumes) display very close IMS drift times while substantially differing in Raman characteristics. Although Raman signals, in general, show significantly better characteristic features than IMS, the Raman spectroscopy alone can have difficulty to identify multiple analytes simultaneously in a mixed sample which is typically the case in field applications. IMS data allows some separation among the components and significantly enhances the processing of the Raman spectra. The integrated display of particle data yielded by these two highly orthogonal detection methods make the determination of the analyte composition more efficient, and reduces the risk of false positives. The Raman shift data illustrated in FIG. 2 is derived from Brian Eckenrode, Edward G. Bartick, Scott D. Harvey, Mark E. Vucelick, Bob W. Wright, Rebecca A., "Portable Raman Spectroscopy Systems for Field Analysis", Huff, Forensic Science Communications, Vol. 3, No. 4 (October 2001), and Process Instruments, "PI-200 Raman Spectrometer Applications" at www.process-instruments-inc.com/pages/energetics.html (last visited on Mar. 10, 2008). The IMS mobility data in FIG. 2 is from Laura M. Matz, Pete S. Tornatore and Herbert H. Hill, Talanta, "Evaluation of suspected interferents for TNT detection by ion mobility spectrometry," pp. 171-179, Vol. 54 (2001) and R. G. Ewing, D. A. Atkinson, G. A. Eiceman, G. J. Ewing, Talanta, "A critical review of ion mobility spectrometry for the detection of explosives and explosive related compounds," pp. 515-529, Vol. 54 (2001).

Figure 6:
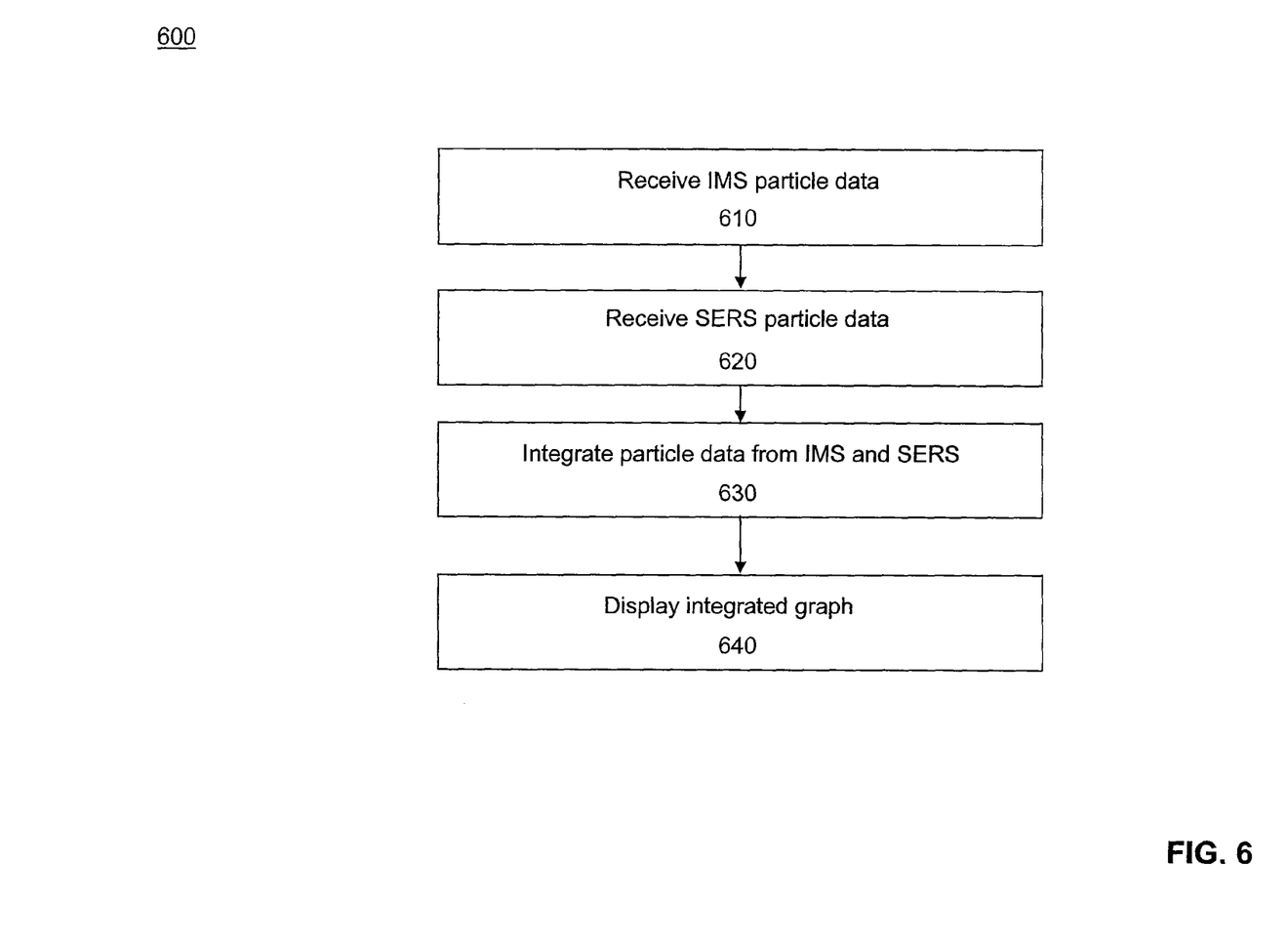
FIG. 6 is a flowchart of steps implemented in a control module to combine the characteristic particle data received from an IMS component and a SERS component of a multi-modal detector according to an embodiment of the present invention.

FIG. 6 illustrates a flowchart 600 that shows, in one embodiment, steps implemented by control module 140 to combine the particle data received from the IMS detector in the first chamber 120 and the SERS detector in the second chamber 130. During or immediately subsequent to the IMS detection phase illustrated in flowchart 400, control module 140 may receive, in step 610, IMS particle data for the analyte sample under consideration. In step 620 control module 140 receives SERS particle data for the analyte sample under consideration. SERS particle data may be collected by control module 140 either during or immediately after the SERS detection phase illustrated in flowchart 500. In step 630 the control module 140 may combine the IMS particle data and the SERS particle data, as they refer to the same analyte compounds. The combined particle data may be illustrated, for example, in a graph 200 designed to differentiate among analyte compounds according to the strength of each detection mechanism. According to some embodiments, in step 640, graph 200 may be displayed in a coupled display 150.

6. Example Computer Embodiment

Figure 7:
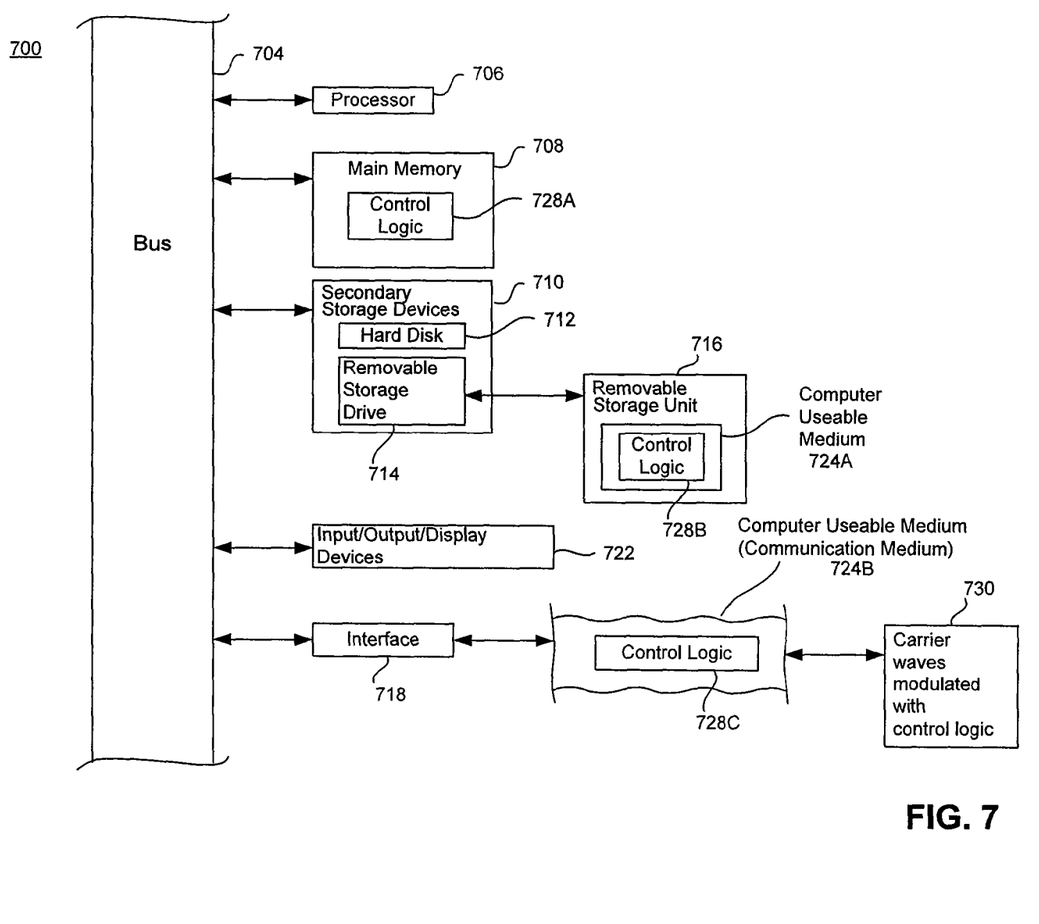
FIG. 7 is an example computer that may implement the system and components of the present invention according to an embodiment.

In an embodiment of the present invention, the system and components of the present invention described herein are implemented using well known computers, such as computer 702 shown in FIG. 7. For example, control module 140 can be implemented using computer(s) 702.

The computer 702 includes one or more processors (also called central processing units, or CPUs), such as a processor 706. The processor 706 is connected to a communication bus 704.

The computer 702 also includes a main or primary memory 708, such as random access memory (RAM). The primary memory 708 has stored therein control logic 728A (computer software), and data.

The computer 702 may also include one or more secondary storage devices 710. The secondary storage devices 710 include, for example, a hard disk drive 712 and/or a removable storage device or drive 714, as well as other types of storage devices, such as memory cards and memory sticks. The removable storage drive 714 represents a floppy disk drive, a magnetic tape drive, a compact disk drive, an optical storage device, tape backup, etc.

The removable storage drive 714 interacts with a removable storage unit 716. The removable storage unit 716 includes a computer useable or readable storage medium 724 having stored therein computer software 728B (control logic) and/or data. Removable storage unit 716 represents a floppy disk, magnetic tape, compact disk, DVD, optical storage disk, or any other computer data storage device. The removable storage drive 714 reads from and/or writes to the removable storage unit 716 in a well known manner.

The computer 702 may also include input/output/display devices 722, such as monitors, keyboards, pointing devices, etc.

The computer 702 further includes at least one communication or network interface 718. The communication or network interface 718 enables the computer 702 to communicate with remote devices. For example, the communication or network interface 718 allows the computer 702 to communicate over communication networks or mediums 724B (representing a form of a computer useable or readable medium), such as LANs, WANs, the Internet, etc. The communication or network interface 718 may interface with remote sites or networks via wired or wireless connections. The communication or network interface 718 may also enable the computer 702 to communicate with other devices on the same platform, using wired or wireless mechanisms.

Control logic 728C may be transmitted to and from the computer 702 via the communication medium 724B. More particularly, the computer 702 may receive and transmit carrier waves (electromagnetic signals) modulated with control logic 730 via the communication medium 724B.

Any apparatus or manufacture comprising a computer useable or readable medium having control logic (software) stored therein is referred to herein as a computer program product or program storage device. This includes, but is not limited to, the computer 702, the main memory 708, secondary storage devices 710, the removable storage unit 716 and the carrier waves modulated with control logic 730. Such computer program products, having control logic stored therein that, when executed by one or more data processing devices, cause such data processing devices to operate as described herein, represent embodiments of the invention.

The invention can work with software, hardware, and/or operating system implementations other than those described herein. Any software, hardware, and operating system implementations suitable for performing the functions described herein can be used.

7. Conclusion

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A particle detection method, comprising:
   (a) detecting a subset of particles of at least one predetermined particle type in an analyte particle sample using a first particle detection mechanism in a first chamber of a particle detector; and
   (b) controlling a shutter between an exit of the first chamber and an entrance of a second chamber of the particle detector, wherein a control module is configured to perform the controlling by opening the shutter in response to said detecting to selectively input only particles of the subset to the second chamber; and
   (c) confirming the presence of the predetermined particle type by using a second particle detection mechanism in the second chamber to analyze only the particles of the subset which are input to the second chamber through said controlled shutter, wherein detection characteristics of the second particle detection mechanism are orthogonal to detection characteristics of the first detection mechanism, and wherein the second particle detection mechanism is activated in response to the detection.

2. The particle detection method of claim 1, wherein the first particle detection mechanism is Ion Mobility Spectroscopy (IMS).

3. The particle detection method of claim 1, wherein the detecting step (Step 1(a)) comprises:
   (i) ionizing the analyte particle sample in the first chamber; and
   (ii) flowing the ionized analyte particle sample through the first chamber.

4. The particle detection method of claim 3, wherein the detecting step (Step 1(a)) further comprises:
   (iv) configuring an electric field in the first chamber to assist flowing of the ionized analyte particle sample.

5. The particle detection method of claim 3, wherein the inputting comprises:
   configuring a shutter grid to permit the ionized analyte particle sample into the first chamber.

6. The particle detection method of claim 1, wherein the second particle detection mechanism is Surface Enhanced Raman Spectroscopy (SERS).

7. The particle detection method of claim 6, wherein the confirming comprises:
   (i) flowing a plurality of ionized particles from the particles of the at least one predetermined particle type into the second chamber;
   (ii) depositing the plurality of ionized particles from the particles of the at least one predetermined particle type on a SERS substrate;
   (iii) irradiating a the SERS substrate with a light source; and
   (iv) detecting Raman signals corresponding to the plurality of ionized particles.

8. The method of claim 1, wherein the controlling further includes closing the shutter upon completion of the detecting of the presence of particles of the at least one predetermined particle type.

9. The method of claim 1, wherein the detecting includes:
   (i) preconfiguring mobility characteristics of the at least one predetermined particle type in the particle detector;
   (ii) determining mobility characteristics of particles of the analyte sample using the first particle detection mechanism; and
   (iii) finding a match between the determined mobility characteristics and the preconfigured mobility characteristics.

10. The method of claim 9, wherein the controlling further includes:
    (i) determining a time interval in which to open the shutter, wherein the time interval is based on the matched preconfigured mobility characteristics; and
    (ii) opening the shutter based on the determined time interval.

11. The method of claim 10, wherein opening the shutter includes:
    electronically opening the shutter based on the determined time interval.

12. The method of claim 7, wherein the confirming further comprises:
    (iv) activating a beam focusing upon the detecting to receive the plurality of ionized particles from the particles of the at least one predetermined particle type into the second chamber.

* * * * *